(12) United States Patent
Fassuliotis et al.

(10) Patent No.: US 8,518,014 B2
(45) Date of Patent: Aug. 27, 2013

(54) SURGICAL SUCTION INSTRUMENT

(76) Inventors: Thomas M. Fassuliotis, Gainesville, GA (US); Ginger E. Lowery, Gainesville, GA (US); John D. Witzigreuter, Canton, GA (US)

( * ) Notice: Subject to any disclaimer, the term of this patent is extended or adjusted under 35 U.S.C. 154(b) by 1683 days.

(21) Appl. No.: 11/586,824

(22) Filed: Oct. 25, 2006

(65) Prior Publication Data

US 2007/0093694 A1 Apr. 26, 2007

Related U.S. Application Data

(60) Provisional application No. 60/729,538, filed on Oct. 25, 2005.

(51) Int. Cl.
*A61M 25/00* (2006.01)

(52) U.S. Cl.
USPC ............ 604/524; 604/523; 604/525; 604/526

(58) Field of Classification Search
USPC ................. 604/523, 524, 525, 526, 527, 530; 433/82, 96; 32/40
See application file for complete search history.

(56) References Cited

U.S. PATENT DOCUMENTS

| | | | |
|---|---|---|---|
| 3,745,655 A * | 7/1973 | Malmin | 433/81 |
| 4,878,900 A | 11/1989 | Sundt | |
| 5,685,836 A | 11/1997 | DiPerna et al. | |
| 6,048,339 A | 4/2000 | Zirps et al. | |
| 6,050,971 A | 4/2000 | Garnier et al. | |
| 6,086,554 A | 7/2000 | Humphreys, Jr. et al. | |
| 6,585,680 B2 | 7/2003 | Bugge | |
| 6,602,072 B2 * | 8/2003 | Burney | 433/96 |
| 6,638,240 B2 * | 10/2003 | Fassuliotis | 604/27 |
| 2006/0024641 A1 * | 2/2006 | Mahlmann | 433/96 |

* cited by examiner

*Primary Examiner* — Kevin C Sirmons
*Assistant Examiner* — Bradley G Thomas, Jr.
(74) *Attorney, Agent, or Firm* — Morgan Law Offices, PLC

(57) ABSTRACT

A surgical suction instrument is provided that is flexible enough to bend in any direction creating a custom shaped suction device. The surgical suction device reduces surgeon fatigue and is rigid enough for use as a retractor. The surgical suction device preferably has the exit suction port below the handle to create a more ergonomic device and reduce user fatigue during surgery.

6 Claims, 5 Drawing Sheets

SURGICAL SUCTION INSTRUMENT

CROSS REFERENCE TO RELATED APPLICATIONS

This application claims the benefit of U.S. Provisional Application Ser. No. 60/729,538, filed by Fassuliotis et al. on Oct. 25, 2005 and entitled "An Improved Surgical Suction Instrument", which is incorporated herein by reference.

FIELD OF THE INVENTION

The present invention relates generally to surgical accessories, and, more particularly, to an improved surgical suction instrument that is flexible enough to bend in any direction creating a custom shaped suction device.

BACKGROUND OF THE INVENTION

It is typically necessary to suction fluids, such as blood, from a surgical site during the course of a surgical procedure. The fluid is suctioned from the surgical site using a surgical suction instrument that is connected to a vacuum pump. The suctioned fluid flows from the surgical suction instrument via tubing to a waste container.

One disadvantage of conventional surgical suction instruments is that they have a rigid shape. This design has the result that an assistant maneuvering the surgical suction instrument is required to be positioned within a small, virtually predetermined area, with respect to the suction or surgical site. This limitation can cause the surgeon to be positioned in an unfavorable position as a compromise to the limitations of the surgical suction instrument. Because the surgical and/or suction site often changes during the course of an operation, delays and mishaps are often encountered as the surgical team is repositioned.

A primary object of the present invention is to provide a surgical suction device that causes less fatigue for the surgeon.

Another object of the present invention is to provide a surgical suction device that is flexible enough to bend in any direction creating a custom shaped suction device.

Another object of the present invention is to provide a surgical suction device that is flexible enough to bend but rigid enough for use as a retractor.

A further object of the present invention is to provide a surgical suction device that has the exit suction port below the handle to create a more ergonomic device and reduce user fatigue during surgery.

Other objects and advantages of the present invention will become apparent from the following descriptions, taken in connection with the accompanying drawings, wherein, by way of illustration and example, an embodiment of the present invention is disclosed.

BRIEF DESCRIPTION OF DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

SUMMARY OF THE INVENTION

Figure 1:
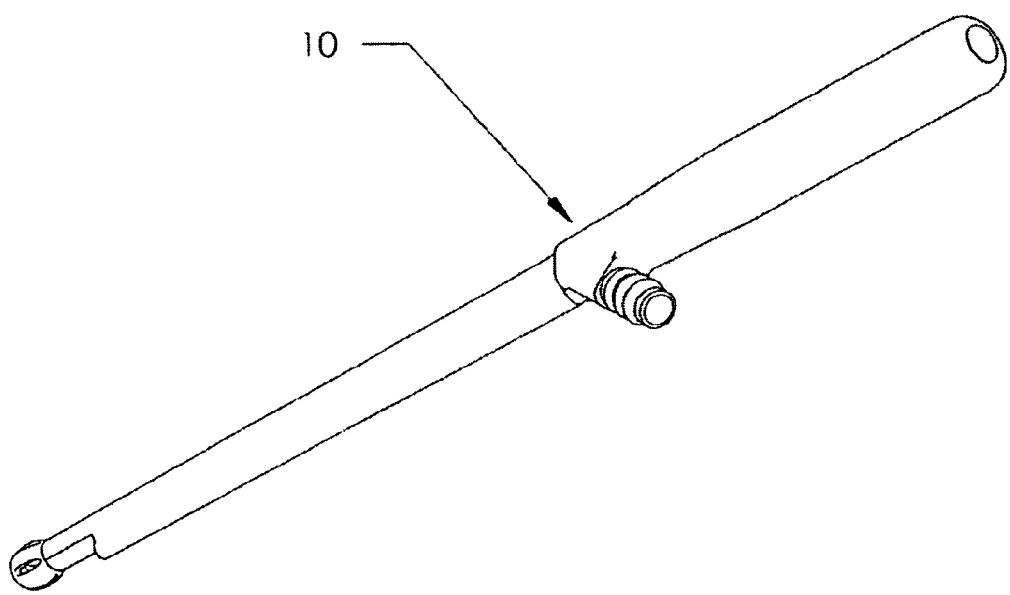
FIG. 1 is a perspective view of a surgical suction device.

A surgical suction instrument is provided that is flexible enough to bend in any direction creating a custom shaped suction device. The surgical suction device reduces surgeon fatigue and is rigid enough for use as a retractor. The surgical suction device preferably has the exit suction port below the handle to create a more ergonomic device and reduce user fatigue during surgery.

According to an aspect of the invention, the surgical suction instrument includes a first section including a suction tip; a second section connected to the first section, the second section bendable to the desired shape; and a third section connected to the second section allowing fluid suctioned from the suction tip, and through the second section, to be removed. The second section is capable of being bent to the desired shape by hand during the course of the surgical procedure (or during preparation for surgery). It is also capable of remaining in the desired shape for a desired period during the course of the surgical procedure to effectively create a custom-shaped suction device.

According to another aspect of the invention, the second section includes a metal rod adjacent to a surgical cavity insertion tube. The metal rod preferably has a diameter greater than about 0.03 inches and less than about 0.18 inches. The metal rod is preferably constructed of stainless steel and about 0.093 inches in diameter.

According to another aspect of the invention, the second section is constructed of a material different from one or more of the first section and the second section. In this case, the metal rod is preferably is insert molded.

According to another aspect of the invention the second section is flexible enough to be bent to 60 degrees out of a plane without breakage.

According to another aspect of the invention, the third section includes a handle. The handle is preferably a hollow handle and includes a handle plug to add rigidity and strength to the handle, and to fill in the hollow handle so as not allow fluids to pass through. Alternatively, the handle could be a single molded part connected to a surgical cavity insertion tube behind a suction tube attachment fitting to direct fluids down the suction tube attachment fitting.

According to another aspect of the invention, the third section includes a suction tube attachment fitting positioned directly in front of the handle. In this case, the suction tube attachment would be positioned at an acute angle (e.g., 45 degree) with the handle.

These and other aspects, features and advantages of the present invention will become apparent from the following detailed description of preferred embodiments, which is to be read in connection with the accompanying drawings.

DETAILED DESCRIPTION OF THE PREFERRED EMBODIMENTS

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

FIG. 1 shows an embodiment of a surgical suction instrument of the present invention generally designated 10.

Figure 2:
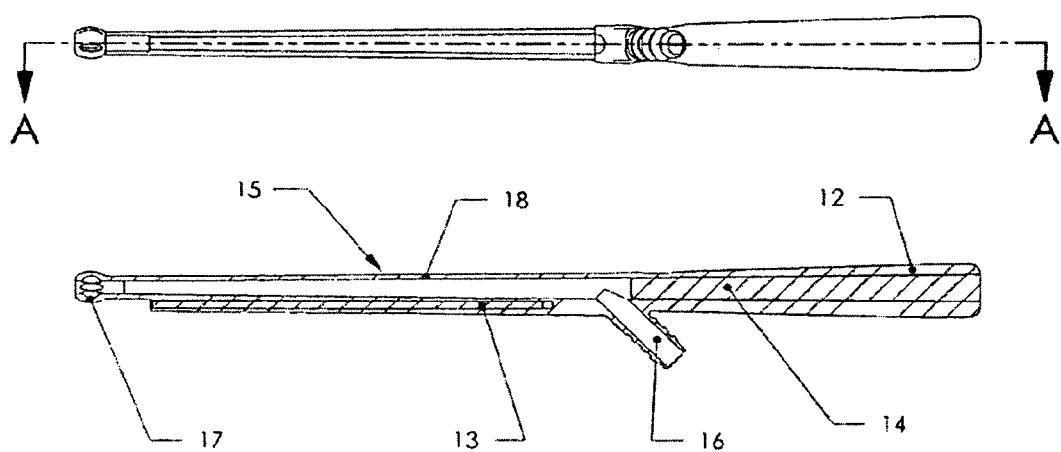
FIG. 2 is a a cross sectional view of the surgical suction device of FIG. 1.

As illustrated in greater detail in FIG. 2, the surgical suction instrument 10 includes a handle 12, a suction tip 17, a suction tube attachment fitting 16, a surgical cavity insertion tube 18, a metal rod 13, and a handle plug 14.

An important function of the handle 12 is to create an ergonomic way for a surgeon to hold onto the surgical suction instrument 10. The handle 12 connects at the very "back end" of the suction instrument 10. In the embodiment shown in FIG. 2, the handle 12 is made hollow. The handle plug 14 is used to add rigidity and strength to the handle 12 and to fill in the (hollow) handle 12 so as not to allow fluids to pass through. An alternative embodiment would be to combine the handle 12 and the handle plug 14 as one molded plastic part. This single part would then connect to the surgical cavity insertion tube 18 behind the suction tube attachment fitting 16 to direct fluids down the suction tube attachment fitting 16.

The suction tube attachment fitting 16 is the connector that a suction tube (not shown) fits over to connect the surgical suction instrument 10 to a vacuum pump (also not shown). The exterior portion of the suction tube attachment fitting 16 preferably includes ridges to help to maintain a tight fit with the suction tube. The suction tube attachment fitting 16 is positioned directly in front of the handle 12. Conventionally, this fitting has been positioned behind (and in parallel with) the handle 12. With the fitting positioned conventionally behind the handle 12 the suction hose many times would get in the way of the surgeon's hands during surgery. By positioning the suction tube attachment fitting 16 in front of the handle, preferably at a 45 degree angle to the suction handle 12, the suction hose advantageously is out of the way allowing the surgeon more freedom during surgery.

In front of the suction tube attachment fitting 16 is the surgical cavity insertion tube 18. This can be a long flexible tube connecting the suction tube attachment fitting 16 with the suction tip 17. A purpose of this insertion tube 18 is to allow a channel for the suction of air and the fluids being removed to communicate back with the suction tube attachment fitting 16 and the suction tube.

The suction tip 17 is attached to the front end of the suction tube attachment fitting 16. The suction tip is preferably round in shape with at least one hole through the center to allow fluids to pass. However, preferably several other openings around the main suction hole are included that are in fluid communication with the central hole. The purpose of the multiple openings is to prevent blockage.

An important aspect of the present invention is the inclusion of the metal rod 13. The metal rod 13 is positioned below, and runs the length of, the surgical cavity insertion tube 18. The purpose of the metal rod 13 is to provide rigidity to the surgical cavity insertion tube 18 once it is bent into shape. It can be seen that the metal rod 13 is situated adjacent to the surgical cavity insertion tube passageway 18. Together these components 13, 18 form a flexible center section 15. Using a metal rod allows the device to be flexible enough to be bent by hand into any orientation yet still be rigid enough to maintain its new shape and be used as a retractor during surgery. The metal rod can be any material that satisfies this function but the preferred material is stainless steel. By sizing the metal rod 13 appropriately (e.g. >0.03 inches in diameter and less than 0.18 inches in diameter, with a preferred diameter for a stainless steel rod being 0.093 inches) the center section 15 can be adjusted into almost any orientation. It is to be understood that the metal rod 13 can be in any desired cross-sectional shape. A preferred shape is one which is round giving equal stiffness to any orientation of bending.

It may be beneficial to make the flexible center section 15 of the surgical suction instrument 10 out of a different material from the rest of the device. It is preferred that the handle 12, suction tube attachment fitting 16 and the suction tip 17 remain rigid during use. It is also preferred that the flexible center section 15 be flexible enough to to be bent up to 60 degrees out of plane without breakage. Therefore, two different materials may be warranted. To accomplish this it may be desirable to use a "two shot injection molding" process. This process allows two different materials to be used to make the part.

A preferred method for constructing the surgical suction instrument 10 with the metal rod 13 adjacent to the surgical cavity insertion tube passageway 18 is to "insert mold" the metal rod. During the molding operation, the metal rod 13 is inserted into a mold before plastic is injected therein. Once the metal rod 13 is inserted, the mold is closed and the plastic is injected around the metal rod 13, forming one part. An alternate method of manufacture would be to mold a blind hole for the metal rod 13 and to insert the metal rod 13 after the plastic portion of the surgical suction device is made. The insert molding method is preferred, however.

An alternate embodiment of the invention would be to allow the suction tube attachment fitting 16 to swivel. This would allow more mobility for the user of the surgical suction device as the suction tube attachment fitting would be less likely to bind or get into the way of the surgeon's hands or arms. This would be accomplished by making the suction tube attachment fitting 16 a separate component and allowing it to rotate in a sealed ball and socket joint.

Figure 3:
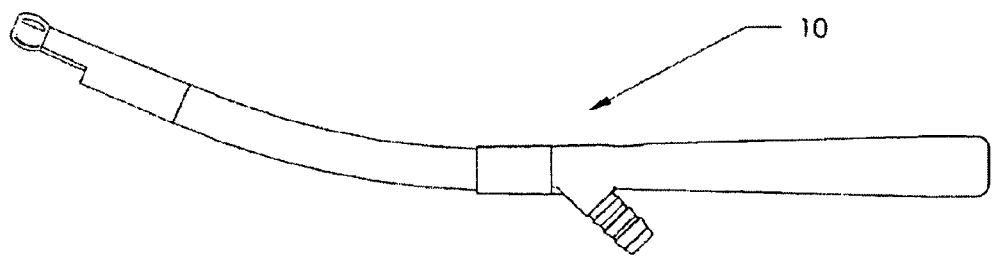
FIG. 3 is a plan view of the surgical suction device showing the suction device positioned upward.
Figure 4:
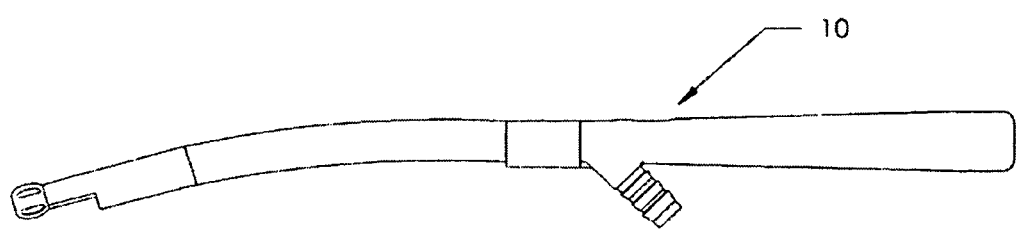
FIG. 4 is a plan view of the surgical suction device showing the suction device positioned downward.
Figure 5:
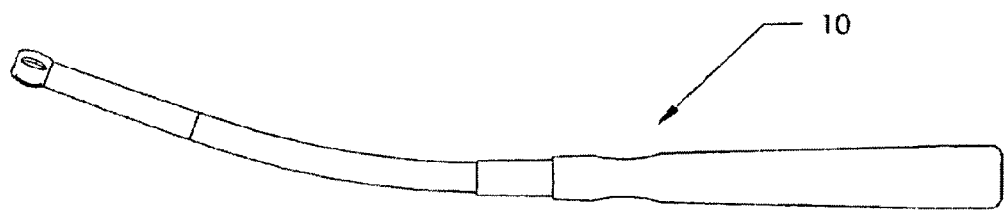
FIG. 5 is a plan view of the surgical suction device showing the suction device positioned to the right side.

FIGS. 3-5 show the surgical suction device 10 in various positions. As can be seen, the surgical suction device 10 can be custom bent to a desired shape creating a custom-shaped suction device.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A surgical suction instrument capable of being bent by hand during a surgical procedure to a desired shape and capable of remaining in the desired shape for a desired period during the course of the surgical procedure to create a custom-shaped suction device, comprising: a first section including a suction tip; a second section connected to the first section, the second section bendable to the desired shape; and a third section connected to the second section allowing fluid suctioned from the suction tip, and through the second section, to be removed; wherein the second section includes a metal rod insert-molded into a surgical cavity insertion tube; and wherein the third section includes a handle and a suction tube attachment fitting positioned directly in front of, and at an acute angle with, the handle; further wherein the handle is a hollow handle and the hollow handle includes a handle plug to add rigidity and strength to the handle, and to fill in the hollow handle so as not to allow fluids to pass through.

2. The surgical suction instrument of claim 1, wherein the metal rod has a diameter greater than about 0.03 inches and less than about 0.18 inches.

3. The surgical suction instrument of claim 1, wherein the metal rod is constructed of stainless steel.

4. The surgical suction instrument of claim 3, wherein the stainless steel metal rod is about 0.093 inches in diameter.

5. The surgical suction instrument of claim 1, wherein the second section is constructed of a material different from one or more of the first section and the third section.

6. The surgical suction instrument of claim 1, wherein the second section is flexible enough to be bent to 60 degrees out of a plane without breakage.

* * * * *